United States Patent [19]

Nakajima et al.

[11] Patent Number: 5,300,067
[45] Date of Patent: Apr. 5, 1994

[54] LASER TREATMENT DEVICE

[75] Inventors: Sadahiro Nakajima; Naoshi Endoh, both of Tokyo; Kenzo Kataoka, Kyoto; Masaki Odaka, Kyoto; Yoshihide Okagami, Kyoto, all of Japan

[73] Assignee: Hoya Corporation, Tokyo, Japan

[21] Appl. No.: 933,083

[22] Filed: Aug. 21, 1992

[30] Foreign Application Priority Data

Aug. 23, 1991 [JP] Japan .................. 3-211837
Nov. 27, 1991 [JP] Japan .................. 3-339761

[51] Int. Cl.$^5$ .............................. A61B 17/36
[52] U.S. Cl. ........................ 606/16; 606/17; 607/89
[58] Field of Search ............. 606/13–18; 604/20, 21; 128/395–398

[56] References Cited

U.S. PATENT DOCUMENTS

| | | | |
|---|---|---|---|
| 4,538,609 | 9/1985 | Takenaka et al. | 606/17 |
| 4,608,980 | 9/1986 | Aihara | 606/18 |
| 4,676,242 | 6/1987 | Doi | 606/16 |
| 4,832,024 | 5/1989 | Boussignac et al. | 128/395 |
| 4,917,084 | 4/1990 | Sinofsky | 606/5 |
| 5,125,058 | 6/1992 | Tenerz et al. | 606/16 |

FOREIGN PATENT DOCUMENTS 0255974 2/1988 European Pat. Off. .............. 606/15

Primary Examiner—Stephen C. Pellegrino
Assistant Examiner—M. Peffley
Attorney, Agent, or Firm—Oliff & Berridge

[57] ABSTRACT

A laser treatment device provided with a laser light source, a laser-light transmitting optical fiber for transmitting laser light output from the laser light source and a probe for guiding the laser light transmitted by the laser-light transmitting optical fiber to an object to be irradiated. Further, the probe is constituted by a laser-light guiding optical fiber separated from the laser-light transmitting optical fiber. Moreover, a cooling chamber for cooling the optical fibers is provided in the neighborhood of an output end of the laser-light transmitting optical fiber, from which the transmitted laser light is output, and an input end of the laser-light guiding optical fiber, from which the laser light output by the laser-light transmitting optical fiber is input to the laser-light guiding optical fiber. Thereby, a medical treatment of a deep part of an affected or diseased region can be achieved without worsening the state of the exit of the laser-light transmitting optical-fiber. Moreover, the output end of the laser-light transmitting optical-fiber can be kept in a favorable condition even after the medical treatment of the deep part of the affected region. Thus there is no obstacle to the next treatment thereof.

11 Claims, 10 Drawing Sheets

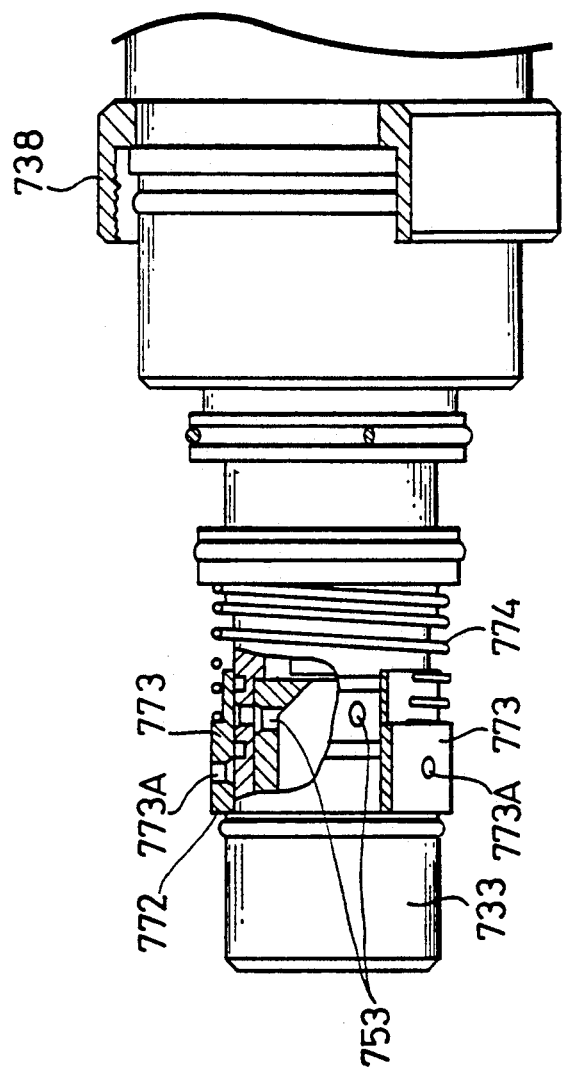

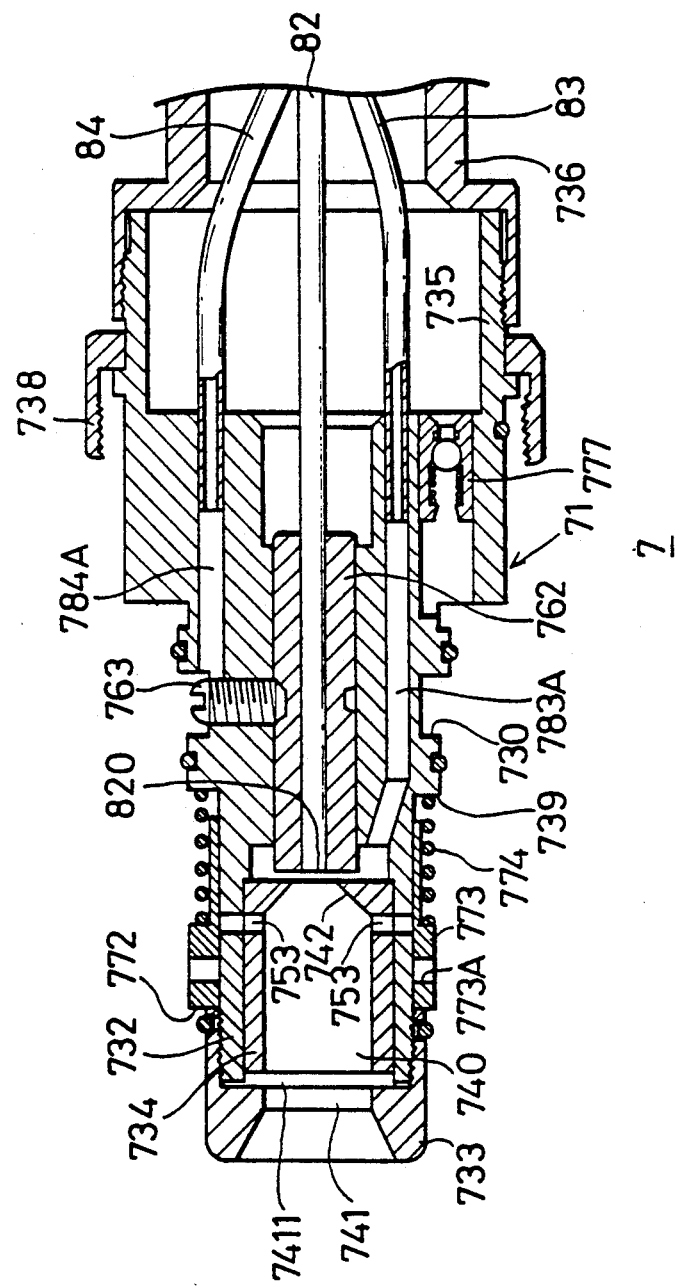

LASER TREATMENT DEVICE

BACKGROUND OF THE INVENTION

1. Field of The Invention

This invention generally relates to a laser treatment device used for a medical treatment to be performed by irradiating laser light, which is transmitted through an optical fiber from a laser light source, on an object and more particularly to a laser treatment device suitable for a medical treatment of a hard tissue (e.g., a tooth) to be irradiated.

2. Description of the Related Art

Generally, in each conventional laser treatment device, a probe for guiding laser light, which is output from an optical fiber for transmitting laser light, to an object to be irradiated is provided at an output end of the optical fiber. Further, there are publicly-known two types of probe. One is a non-contact type of probe as disclosed in, for example, Japanese Unexamined Patent Publication (Kokai Tokkyo Koho) Official Gazette No. 61-20544, which does not contact an object to be irradiated. The other is a contact type of probe as disclosed in, for instance, Japanese Unexamined Patent Publication (kokai Tokkyo Koho) Official Gazette No. 63-318934, which contacts an object to be irradiated.

A probe of the non-contact type is operative to irradiate laser light output (namely, emitted) from the output end of the optical fiber on the object by converging the output laser light on a spot having a predetermined spot size thereon. Further, a probe of the contact type is formed as an individual device other than the optical fiber by using, for example, a sapphire rod and abrading (namely, tapering) the sapphire rod in such a manner that the diameter of the transverse section of the probe becomes smaller gradually toward one end thereof. Furthermore, the laser light output from the output end of the optical fiber impinges on the probe of this type and thereafter undergoes an internal reflection on an abraded surface. As the result, the reflected laser light is converged on an end portion of the probe of this type and is then irradiated on the object by bringing the end portion of this probe into direct contact with the object.

Incidentally, in case of another laser treatment device manufactured by, for example, Laserscope Inc. of U.S.A., an output portion of an optical fiber for transmitting laser light is used as a probe of the contact or non-contact type.

Additionally, in recent years, an Er:YAG laser (namely, $E_r{}^{3+}$ laser) has been developed as a laser light source, by which a hard tissue, as well as a soft tissue, can be processed. Consequently, a laser treatment device can be used for a medical treatment of dentin (or dentinum) or enamel by employing such a laser.

The aforesaid conventional laser treatment devices, however, have encountered the following problems.

First, the diameter of the converging lens employed in the probe of the non-contact type is at least 1 millimeter (mm) Φ or so. Namely, it is difficult to make a probe of this type, the converging lens of which is less than 1 mm Φ in diameter. Thus, in case of a medical treatment of the inside of a narrow diseased region (for example, a crooked root canal, which is not more than 500 microns (μm) Φ in diameter, or a periodontal concavity (i.e., a periodontal pocket)), a deep part of the diseased region cannot be sufficiently irradiated with laser light.

Moreover, although an end of an ordinary probe of the contact type is 0.3 mm Φ in outer diameter or so, a base of the tapered portion thereof is thick and 2 mm Φ or so in outer diameter. Therefore, similarly as in case of the probe of the non-contact type, a deep part of an affected region cannot be sufficiently irradiated with laser light.

In contrast, in case where the output end of the optical fiber is used as a probe, even a deep part of an affected or diseased region can be sufficiently processed. However, in case of such a type of probe, the output end of the optical fiber may melt due to heat produced at the time of irradiation. Further, matters scattered at the time of irradiation sometimes adhere to the output end of the optical fiber. Moreover, the output end of the optical fiber, to which the scattered matters adhere, may melt as a result of being heated by laser light. Such a melting of the output end of the optical fiber and an adhesion of the scattered matters thereto result in that the intensity of laser light output therefrom becomes uneven and the performance of the probe becomes deteriorated and that additionally, after such an output end of the optical fiber is used as a probe, it becomes impossible to perform a medical treatment of soft tissues by fitting an ordinary probe of the contact type made of sapphire or the like, which has been separated from the optical fiber, to such an output end thereof.

Further, especially in case of performing a medical treatment of hard tissues such as dentin by using an Er:YAG laser, it is preferable for effectively preventing vaporized matters, which are generated at the time of performing the medical treatment, from adhering to dentin or the like to spurt washing water from the vicinity of a probe simultaneously with outputting laser light. However, there has been raised a problem that an optical fiber including a fluoride (hereunder sometimes referred to as a fluoride fiber), which can efficiently transmit laser light output from an Er:YAG laser, is liable to influence of water or moisture.

SUMMARY OF THE INVENTION

The present invention is created to solve the problems, which are described hereinabove, of the conventional laser treatment devices.

It is, accordingly, a first object of the present invention to provide a laser treatment device which can irradiate laser light on a deep part of an affected or diseased region easily and surely for the purpose of, for instance, performing a medical treatment of a root canal of a tooth, removing tartar and caries and forming a cavity in a tooth.

Further, it is a second object of the present invention to provide a laser treatment device which can prevent an output end of an optical fiber thereof from melting, thereby securing a light-guiding function intrinsic to the optical fiber and replacing one of probes of the various kinds with another.

Moreover, it is a third object of the present invention to provide a laser treatment device which can spurt washing water from the vicinity of a probe without influence of water or moisture on an optical fiber even in case of employing an optical fiber of a kind, which is liable to the influence of water or moisture, as an optical fiber for transmitting laser light.

To achieve the foregoing object, in accordance with the present invention, there is provided a laser treatment device which comprises a laser light source, a laser-light transmitting optical fiber for transmitting laser light output from the laser light source and a probe for guiding the laser light transmitted by the laser-light transmitting optical fiber to an object to be irradiated, wherein the probe is constituted by a laserlight guiding optical fiber separated from the laserlight transmitting optical fiber, and wherein a cooling chamber for cooling the optical fibers is provided in the neighborhood of an output end of the laser-light transmitting optical fiber, from which the transmitted laser light is output, and an input end (namely, an incidence or entrance end) of the laser-light guiding optical fiber, from which the laser light output by the laser-light transmitting optical fiber is input to the laser-light guiding optical fiber.

Thereby, a medical treatment of a deep part of an affected or diseased region can be achieved without worsening the state of the exit of the laser-light transmitting optical-fiber. Moreover, because the output end of the laser-light transmitting optical-fiber is cooled by the cooling chamber, the output end of the laser-light transmitting optical-fiber can be kept in a favorable condition even after the medical treatment of the narrow or deep diseased region. Thus there is no obstacle to the next treatment thereof.

Further, in case of an embodiment of the aforesaid laser treatment device of the present invention, the input end of the probe (namely, the input end of the laser-light guiding optical fiber) is projected or protruded from an inner surface of the cooling chamber.

Thereby, even if a part of laser light emitted from the output end of the laser-light transmitting opticalfiber does not enter the input end of the probe, but reaches the inner surface of the cooling chamber, the inner surface thereof is not damaged, nor is generated any vaporized matter. This is because the energy flux density of the laser light which has reached the inner surface thereof becomes low. Additionally, the cooling of the input end of the probe can be facilitated.

Moreover, in case of another embodiment of the aforesaid laser treatment device of the present invention, the outer diameter of the input end of the probe is set as equal to or less than that of the output end of the laser-light transmitting optical-fiber.

Thereby, a probe, which is thinner than the laserlight transmitting optical-fiber, can be used. Consequently, a medical treatment of a narrower portion can be achieved.

Furthermore, in case of a further embodiment of the aforesaid laser treatment device of the present invention, a transparent or transmittable member is provided between the input end of the probe and the output end of the laser-light transmitting optical-fiber. Additionally, in this embodiment, the cooling chamber is partitioned into a first cooling sub-chamber for cooling the input end of the probe and a second cooling chamber for cooling the output end of the laser-light transmitting optical-fiber. Thus the input end of the probe and the output end of the laser-light transmitting optical-fiber can be cooled by using different refrigerants independently of each other.

Thereby, laser light can be made to impinge on the input end of the probe from the output end of the laser-light transmitting optical-fiber through the transparent member. Moreover, two cooling sub-chambers, which are independent of each other, can be formed by partitioning off the input end of the probe from the output end of the laser-light transmitting optical-fiber by use of the transparent or transmittable member. Thus the input end of the probe and the output end of the laser-light transmitting optical-fiber can be cooled independently of each other by using different refrigerants. Therefore, in case where, for instance, an optical fiber of a type, which is liable to the influence of water or moisture, is employed as the laser-light transmitting optical-fiber, the cooling sub-chamber for cooling the output end of the laser-light transmitting optical-fiber is cooled by using dry gas independently of the cooling sub-chamber for cooling the input end of the probe in such a manner to prevent the laser-light transmitting optical-fiber from being affected by water or moisture. On the other hand, the cooling sub-chamber can be cooled by using another cooling system. Thus, even in case where the probe is detachably fitted to the laser-light transmitting optical-fiber (namely, the probe is exchangeable) as in case of the foregoing embodiment, the output end of the laser-light transmitting optical-fiber can be prevented from being exposed to a moist outer or open air.

Further, in case of still another embodiment of the aforesaid laser treatment device of the present invention, a light-converging member for converging laser light output from the output end of the laser-light transmitting optical-fiber to the input end of the probe is employed as the transparent or transmittable member.

Thereby, the transparent or transmittable member, which is constituted by the light-converging member, can have both of the function of partitioning the cooling chamber into two cooling sub-chambers and the function of converging and inputting laser light emitted from the output end of the laser-light transmitting optical-fiber to the input end of the probe.

Moreover, in case of yet another embodiment of the aforesaid laser treatment device of the present invention, a third cooling chamber for cooling an input end of the laser-light transmitting optical fiber is further provided in the neighborhood of the input end of the laser-light transmitting optical fiber.

Thereby, the input end of the laser-light transmitting optical-fiber can be prevented from being damaged due to heat when laser light input from the laser light source thereto.

Furthermore, in case of another embodiment of the aforesaid laser treatment device, a liquid guiding member for letting liquid flow along the probe and spurting the liquid from the vicinity of an end of the probe is further provided in such a manner to cover an outer peripheral portion of the probe. In addition, a liquid feeding member for supplying liquid to the liquid guiding member is also provided in this embodiment.

Thereby, a lavage of an object of a medical treatment can be achieved. Moreover, the probe can be cooled.

Besides, in case of a further embodiment of the present invention, a probe angle regulating member for turning the probe in an arbitrary direction and holding the probe in a state, in which the probe is turned in such a direction, is provided on an outer exposed surface of the probe.

Thereby, the probe can be appropriately angled according to the contents of a medical treatment. Thus a medical treatment of an affected part (for instance, the back of a tooth), which is hard for the treatment device to irradiate with laser light, can be achieved easily and surely.

Further, in case of still another embodiment of the aforesaid laser treatment device of the present invention, an Erbium ion laser is employed as the laser light source.

Thereby, hard tissues such as a tooth can be surely achieved.

Moreover, in case of yet another embodiment of the present invention, the probe is detachably provided to the laser-light transmitting optical-fiber.

Thereby, the probe can be suitably selected and exchanged according to the purpose of a medical treatment. Consequently, the medical treatment can be accomplished efficiently and surely.

BRIEF DESCRIPTION OF THE DRAWINGS

Other features, objects and advantages of the present invention will become apparent from the following description of preferred embodiments with reference to the drawings in which like reference characters designate like or corresponding parts throughout several views, and in which:

FIG. 13 is a partially cutaway fragmentary-side-view of the connector portion 7 of FIG. 7; and FIG. 14 is a partial longitudinal sectional view of the connector portion 7 of FIG. 7.

DETAILED DESCRIPTION OF THE PREFERRED EMBODIMENTS

Hereinafter, preferred embodiments of the present invention will be described in detail by referring to the accompanying drawings.

1. First Embodiment

Figure 1:
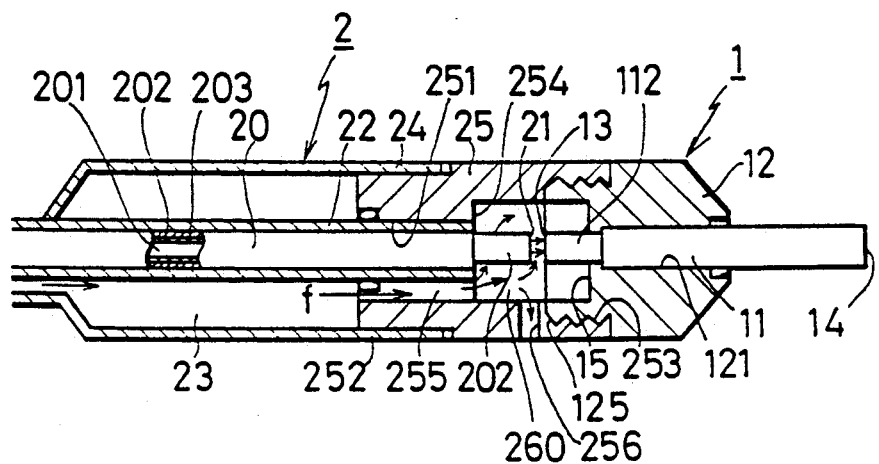
FIG. 1 is a sectional view of a laser hand part (hereunder referred to as a laser hand piece) provided at an end portion of a laser-light transmitting opticalfiber of a laser treatment device (hereunder sometimes referred to as a first embodiment) embodying the present invention.
Figure 2:
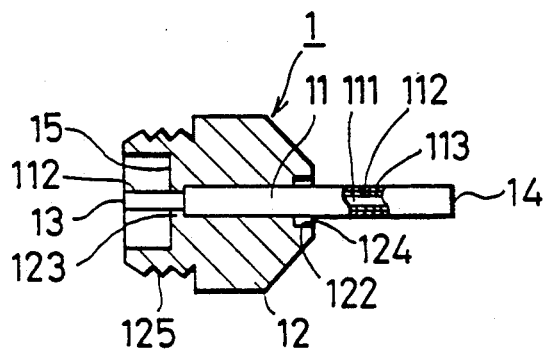
FIG. 2 is a sectional view of a probe device of what is called a fiber type fitted to the laser hand piece of FIG. 1.

Referring first to FIG. 1, there is sectionally illustrated the configuration of a laser hand piece provided at an end of a laser-light transmitting optical-fiber led from a laser light source of a first embodiment of the present invention, namely, a laser treatment device of the present invention. Referring next to FIG. 2, there is sectionally illustrated the structure of a probe device of the fiber type to be fitted to the laser hand piece of FIG. 1. Hereinafter, the first embodiment of the present invention will be described in detail by referring to these figures.

In FIGS. 1 and 2, reference numeral 1 designates a probe of the fiber type; and 2 a laser hand piece, to which the probe device 1 of the fiber type is detachably fitted.

Roughly speaking, the probe device 1 of the fiber type consists of a fiber probe 11, which serves as a probe for directly guiding laser light to a hard object (e.g., a tooth) to be irradiated, and a male connector portion 12 which supports the fiber probe 11 and is fitted to the laser hand piece 2.

The fiber probe 11 is constituted by an ordinary optical fiber, in which a cladding 112 is formed around a core 111 and further the cladding 112 is coated with a protective jacket 113. As viewed in these figures, on the right side of the fiber probe 11 corresponding to the tip thereof, the cladding 112 is coated with the protective jacket 113 to the right end (namely, a laserlight outputting end (hereunder sometimes referred to simply as an output end)) thereof. On the other hand, on the left side of the fiber probe 11 corresponding to the root or base (namely, a laser-light inputting end (hereunder sometimes referred to simply as an input end)) thereof, a part of the cladding 112, which is extended into a first cooling concave portion 15, is exposed by peeling off the protective jacket 113. The end surface of the root (namely, the input end) 13 of the fiber probe 11 is abraded. Further, the end surface of the tip (namely, the output end) 14 of the fiber probe 11 is also abraded. However, if the broken or cut surface (namely, the fracture) of the output end of the fiber probe 11 at the time of manufacturing the device is used as the end surface 14 thereof, the use of the fiber probe 11 is not hindered. The length of the fiber probe 11 is suitable established according to the use of the device. Incidentally, the reason for extending the exposed part of the cladding 112 into the first cooling concave portion 15 is as follows. Namely, even in case where a part of laser light emitted from the output end 21 of an optical fiber 20 does not enter the input end 13 of the fiber probe 11, but leaks out of the fiber probe 11, if the exposed part of the cladding 112 is extended into the first cooling concave portion 15, the energy flux density of the leaked part of the laser light can be decreased when the leaked part of the laser light impinges on the inner wall of the concave portion 15, and thus the leaked part of the laser light can not vaporize the inner wall of the portion 15. Moreover, a cooling of the cladding by using cooling fluid f (to be described later) can be efficiently performed.

Further, an optical fiber capable of transmitting laser light to be used may be employed as the fiber for use in the fiber probe 11. In case of using, for example, laser light output from an Er:YAG laser, which oscillates at the wavelength of 2.94 μm, a glass fiber (e.g., a fluoride fiber, a chalcogenide glass fiber, a dehydrated silica glass fiber), as well as a crystal fiber (e.g., a sapphire fiber, a zinc selenide fiber), may be employed as the fiber for use in the fiber probe 11. Incidentally, in case of this embodiment, a fluoride fiber is used as the fiber probe 11. Further, the outer diameter of the core 111 and that of the cladding 112 are set as 430 μm and 450 μm, respectively. Furthermore, a gold evaporation is effected such that the outer diameter of the protective jacket 13 becomes equal to 480 μm.

It is preferable to use a material, which has good heat-resistance and large mechanical strength, as the material of the protective jacket 13 so that the jacket 13 can be used in case of a medical treatment of a hard tissue like a tooth. Thus, a metal other than gold (e.g., aluminum) or an organic material (e.g., a polyamide resin) may be employed as the material of the protective jacket 13. Further, a nonelectrolyte plating is employed as a method for forming the jacket 13, instead of the evaporation. Alternatively, the jacket 13 may be formed by fabricating a preform by use of the material of the jacket and directly drawing the preform into a fiber.

In the central portion of the male connector portion 12, a hole 121, to which the base of the fiber probe 11 is inserted and fixed, is bored. Further, a groove, into which an O-ring is inserted, is formed at the outer end of the hole 121 (namely, the right end thereof as viewed in FIG. 2). At the opposite inner end of the hole 121, a positioning stage 123 is formed in such a manner that the inner diameter of the stage 123 is less than the diameter of the hole 121. Further, the positioning of the fiber probe 11 is performed by being inserted into the hole 121 and letting the exposed portion of the cladding 112 through the central hole of the stage 123 and also letting the protective jacket 113 touch the stage 123. Thus, in such a state, the fiber probe 11 is fixed to the male connector portion 12 by using an adhesive or by being fitted thereto. Incidentally, an 0@ring 124 is fitted to the groove 122 at the outer end of the hole 121.

As shown in FIG. 1, the first cooling concave portion 15 is formed on the left side (namely, the inner side) of the male connector portion 12. This portion 15 serves to form a space, into which the cooling fluid f flows, around the exposed portion of the cladding 112 protruding from the hole 121, thereby cooling the cladding 112. Incidentally, a dry fluid (e.g., a dry air), which serves to cool the cladding and eliminate moisture contained in the air within the space or ventilation path of the fluid f, is employed as the cooling fluid f. This is because the fluoride fiber has a weak moisture-resistance.

Further, a screw thread is formed on the outer surface of an end part of the male connector portion 12 corresponding to the concave portion 15 thereof and is joined with a helical groove (namely, a female screw) 253 of the laser hand piece 2 (to be described later), thereby forming a cooling chamber 260 (to be also described later) and connecting the laser hand piece 2 with the probe device of the fiber type 1 optically.

In FIG. 1, reference numeral 20 denotes the laserlight transmitting optical-fiber for transmitting laser light emitted from a laser light source (not shown) to the probe device 1 of the fiber type. Similarly as in case of the fiber probe 11, a fluoride fiber comprised of a core 201, a cladding 202 and a protective jacket 203 is employed as the laser-light transmitting optical fiber 20. Incidentally, the outer diameters of the core 201, the cladding 202 and the protective jacket 203 are 400, 450 and 500 μm, respectively. Additionally, the protective jacket 203 is constituted by a UV (ultraviolet radiation) acrylic jacket. Further, an optical fiber capable of transmitting laser light to be used may be employed as the laser-light transmitting optical fiber 20. In case of using, for instance, laser light output from an Er:YAG laser, which oscillates at the wavelength of 2.94 μm, a glass fiber (e.g., a fluoride fiber, a chalcogenide glass fiber, a dehydrated silica glass fiber), as well as a crystal fiber (e.g., a sapphire fiber, a zinc selenide fiber), may be employed as the fiber for use in the laser-light transmitting optical-fiber 20.

Roughly speaking, the laser hand piece 2 is composed of a stainless capillary 22, the mechanical strength of which is assured by accommodating the laser-light transmitting optical fiber 20 therein, and an outer tube 24, which accommodates the capillary 22 therein in such a manner to be separated therefrom by a constant interval and to form a space serving as the ventilation path or passage of the fluid f, and an end-fixing metal fitting 25 fitted to an end of the outer tube 24 for holding and fixing the capillary 22 and the outer tube 24 at a regular interval.

Further, a tip portion of the laser-light transmitting optical fiber 20 (namely, the right end of the fiber 20 as viewed in FIG. 1), at which a cladding 202 is exposed by peeling off the protective jacket 203, is protruded in a second cooling concave portion 264. In the central portion of the fitting 25, a hole 251, into which the capillary is inserted, is pierced. Moreover, on the base side of the fitting 25 (namely, on the left side of the fitting 25 as viewed in FIG. 1), a connecting portion 252 to be used for inserting the fitting 25 into the outer tube 24 is formed on the outer surface thereof. The exposed portion of the cladding 202 of the fiber 20 accommodated in the capillary 22 is protruded to the concave portion 254 and supported at an accurate position by inserting the capillary 22 into the hole 251 and fixing the capillary 2 thereto. Further, as is seen from FIG. 1, the exposed portion of the cladding 202 is face to face with that of the cladding 112 and 202 (namely, the exposed portions of the claddings 112 and 202 are aligned in a line) by connecting the probe device 1 of the fiber type to the input end of the fiber probe 11.

Incidentally, the reason for protruding the exposed portion of the cladding 202 into the concave portion 254 is as follows. Namely, a part of laser light emitted from the output end 21 of the optical fiber 20 is sometimes reflected and returned thereto. The reflected laser light should not go back to the laser light source and thus should be prevented from impinging on the output end 21 of the fiber 20. Moreover, there is necessity of performing a cooling by using the fluid f efficiently.

Furthermore, the female screw 253, which should be joined with screw thread 125 of the probe device 1 of the fiber type, is formed on the tip or right end of the fitting 25. Further, the second cooling concave portion 254 for cooling the exposed portion of the cladding 202 by forming a space, into which the cooling fluid f can flow, around such a portion of the cladding 202 is formed in the screw 253. Moreover, a through hole 255 is formed between the ventilation path 23 and the concave portion 254, which is partitioned off from the path 23 by the fitting 25, but is open to the path 23 through the hole 255. Additionally, an exhaust hole 256 for exhausting the cooling fluid f, which flowed into the concave portion 254, to the outside and for letting the concave portion 254 communicate with the outside is formed in the fitting 25.

Further, the cladding 202 of the laser-light transmitting optical fiber 20 is aligned with the cladding 112 of the fiber probe 11 by joining the thread screw 125 formed on the male connector portion 12 of the probe device 1 of the fiber type with the groove 253 of the fitting 25. Thus the output end 21 of the cladding 202 is aligned with the input end 13 of the cladding 112. Thereby, laser light transmitted from the laser light source is efficiently led to the fiber probe 11. Moreover, the cooling chamber 260 is constituted by the first cooling concave portion 15 and the second cooling concave portion 254, which are formed around the aligned claddings 112 and 202, respectively.

Incidentally, an Er:YAG laser is employed as a laser light source.

In the laser treatment device having the above described configuration, laser light emitted from the laser light source is transmitted to the laser hand piece 2 through the laser-light transmitting optical-fiber 20. This laser light is emitted from the output end 21 of the optical fiber 20 in the laser hand piece 2. Then, this laser light is incident on the input end 13 of the fiber probe 11 of the probe device 1 of the fiber type. Thereafter, the laser light entered the fiber probe 11 is led to a destination by the fiber probe 11 and is irradiated to an object.

At that time, the cooling fluid f is fed from the side of the laser light source to the laser hand piece 2 through the ventilation path 23. When reaches this laser hand piece 2, the fluid f is supplied to the cooling chamber 260 through the hole 255. While cooling the portions of the claddings 112 and 202 protruded to the chamber 260, the fluid f is dried. Finally, the dried fluid f is exhausted through the hole 256 to the outside.

Thereby, the laser-light transmitting optical fiber 20 can be prevented from being damaged due to moisture. Moreover, the output end 21 of the cladding 112 and the input end 13 of the cladding 202 can be surely prevented from being heated and dissolved. Furthermore, the neighborhood of the input end 13 of the cladding 202 can be prevented from being overheated by laser light leaked thereto, which is not incident on the input end 13 of the cladding 202. In addition, the irradiation of laser light to the narrow or deep part of a diseased region can be facilitated.

Figure 3:
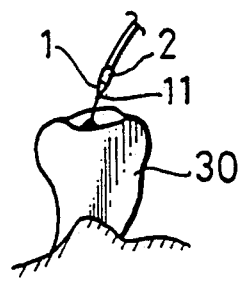
FIG. 3 is a diagram for illustrating how a dental treatment is per-formed by using the first embodiment of FIGS. 1 and 2.

FIG. 3 is a diagram for illustrating how a dental treatment of a tooth 30 is effected by using this embodiment of the present invention (namely, the laser treatment device of the present invention). As illustrated in this figure, the probe device 1 of the fiber type is fitted to the laser hand piece 2. Further, the fiber probe 11 is inserted in the tooth 30. Subsequently, the output end (14) of the fiber probe 11 is aimed at a focus of the diseased region and then laser light is irradiated on the diseased region.

In this case, when matters scattered from the tooth 30 as the result of the irradiation of laser light thereon adhere to a part of the output end 14 of the fiber probe 11 or a part of the output end 14 thereof dissolves due to heat produced at the time of the irradiation of laser light on the tooth 30, the part of the output end 14, to which the scattered matters have adhered, or the dissolved portion thereof is eliminated by abrading such a part or portion of the output end 14. Upon completion of the elimination of the scattered matters or dissolved portion from the output end 14, the irradiation of laser light having the same energy as in case of the last irradiation is resumed.

Furthermore, the output end 14 is sometimes abraded by being touched by the hard tissue, namely, the tooth 30. However, note that the fiber probe 11 is an optical fiber. Therefore, if the probe 11 is cut at a given point thereof, output laser light having substantially the same property can be obtained. Thus, even in case where the output end 14 is abraded by the hard tissue, output laser light having characteristics as designed originally can be obtained.

Figure 4:
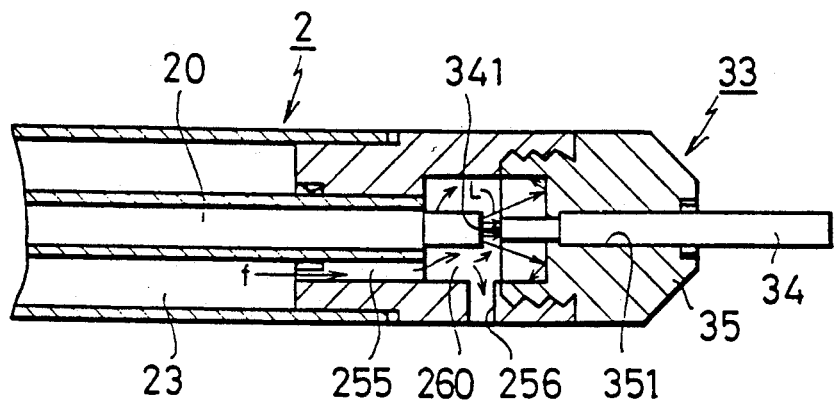
FIG. 4 is a sectional view of an example o-f the laser hand piece, to which a fiber probe (to be described later) having a relatively small diameter is fitted.

In contrast, when a medical treatment of the inside of a narrow diseased region (for example, a crooked root canal, or a periodontal concavity) or a deep part of the diseased region is carried out, an optical fiber, the outer diameter of which is less than the fiber 20, is used as a fiber probe 34 of a probe device 33 of the fiber type, as illustrated in FIG. 4. Namely, the probe device 33 of the fiber type incorporating the fiber probe 34, which employs such a thinner optical-fiber, is fitted to the laser hand piece 2. Then, laser light is irradiated on an object by using this thinner fiber probe 34. Incidentally, the structure of the probe device 33 of the fiber type is similar to that of the probe device 1 except that the outer diameter of the fiber probe 34 and the inner diameter of a hole 351 of a male connector portion 35 is smaller in comparison with the corresponding elements of the probe device 1. Additionally, the diameter, length and shape of the fiber probe 34 may be established according to the purpose of a medical treatment. Thus a medical treatment suitably corresponding to the various condition (e.g., crookedness and depth) of a diseased region can be achieved by selecting suitable one of the probe devices 33 respectively employing the fiber probes 34 preset in the various manners as described above and by appropriately exchanging the currently used probe device with the selected one.

Thereby, such a suitable fiber probe can be easily inserted into a region which is narrow to the extent that the fiber probe 11 having the same diameter as the optical fiber 20 does cannot be inserted. Consequently, an object can be surely irradiated with laser light.

Further, in this case, not all of laser light L emitted from the output end 21 of the laser-light transmitting optical-fiber 20 cannot enter the fiber probe 33. Namely, a part of the laser light L misses an input end 341 of the fiber probe 34 and is irradiated on the inner wall of the first cooling concave portion 15.

The inner wall of the concave portion 16, however, is apart from the output end 21 of the optical fiber 20 a regular distance. Therefore, when the laser light reaches this inner wall, the energy flux density of the laser light becomes small. Moreover, the cooling fluid f flows through the cooling chamber 260. As the results, the neighborhood of the concave portion 15 can not be overheated by the irradiated laser light.

Thereby, an occurrence of thermal breakage of the laser-light transmitting optical fiber 20 and the fiber probe 34 can be prevented. Further, the protective jackets can be prevented from being overheated, destroyed by fire and fractured. Moreover, an occurrence of thermal breakage of the fiber 20 and the fiber probe 33 due to the adhesion of scattered matters to the end surfaces thereof can be prevented.

Incidentally, in case of this embodiment, the inner diameter of the cooling chamber 260 is greater than the outer diameter of the capillary 22 in which the optical fiber 20 is accommodated. Further, the length of the cooling chamber 260 is nearly equal to the total length of the exposed portions of the claddings 202 and 112. Furthermore, the size of the cooling chamber 260 is established in such a manner that the cooling fluid f can flow around and cool the claddings 202 and 112 sufficiently. In addition, the output end 21 of the optical fiber 20 and the input end 13 of the fiber probe 11 should be apart from each other a predetermined distance.

Further, an exhaust path to be used for exhausting the fluid f therethrough instead of using the hole 256 provided to the cooling chamber 260 may be provided in the laser hand piece in addition to the hole 255.

Figure 5:
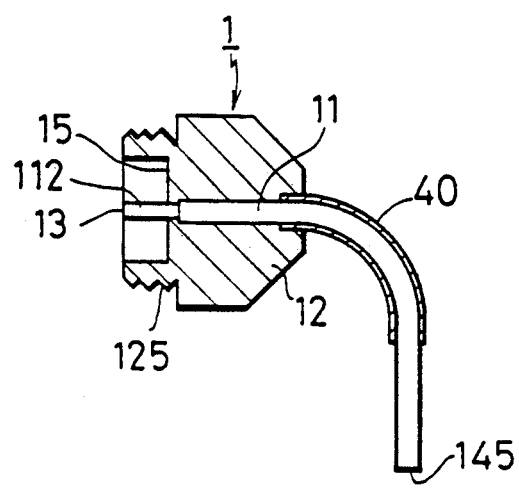
FIG. 5 is a sectional view of an example of the fiber probe, to which a thin tube (hereunder referred to as a capillary) for regulating a bend angle, at which the fiber probe is bent, is fitted.

Moreover, in case of this embodiment, an optical fiber is used as each of the fiber probes 11 and 34 respectively provided in the probe devices 1 and 33 of the fiber type. However, as shown in FIG. 5. An angled regulating capillary 40 for regulating a bend angle of a probe may be provided to each of the probes 11 and 34. This capillary 40 is made of flexible metal and shaped like a tube. The elasticity of the capillary 40 is set as greater than that of each of the probes 11 and 34. Thus, each of the probes 11 and 34, the bend angle of which is regulated by bending the capillary 40, does not get loose due to its elasticity. Further, the capillary 40 is fixed to the male connector portion 12 at the base thereof in a state where the probe 11 or 34 is inserted therein. Each of the fiber probe 11 and 34 can be oriented at a predetermined angle with respect to the male connector portion 12 by bending the capillary 40.

Thereby, the fiber probes 11 and 33 bent in this way can easily reach a diseased part (e.g. , the back of a tooth) which is hard to be treated. Consequently, even such a diseased part can be surely treated.

Moreover, in case of this embodiment, the probe device 1 of the fiber type is detachably fitted to the laser hand piece 2 by joining the male and female screws with each other. Alternatively, another suitable means (e.g., a well-known bayonet coupling using a spring) may be employed.

Figure 6:
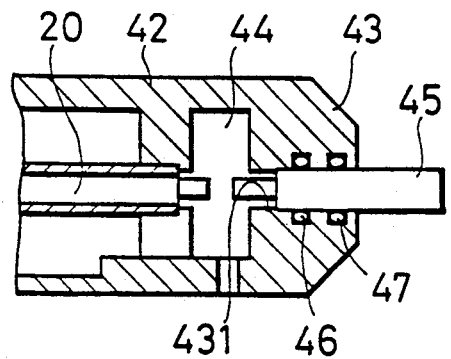
FIG. 6 is a sectional view of an example of the laser hand piece incorporated with a male connector portion.

Furthermore, in case of this embodiment, the application thereof to various purposes of medical treatments can be realized by using a plurality of probe devices of the fiber type, each of which has a male connector portion to which a fiber probe is fitted as a probe. As illustrated in FIG. 6, a laser hand piece 42 and a male connector portion 43 may be formed as one body. In addition, a cooling chamber 44 may be formed between the laser hand piece 42 and the male connector portion 43. Further, a fiber probe 45 is inserted into a hole 431 bored in the male connector portion 43 and is supported by two 0-rings 46 and 47 fitted into the hole 431. Thus, the detachment and exchange of the probe device can be facilitated by making only the fiber probe detachable as stated hereinabove. Consequently, reduction in cost of the laser treatment device can be achieved.

2. Second Embodiment

Figure 7:
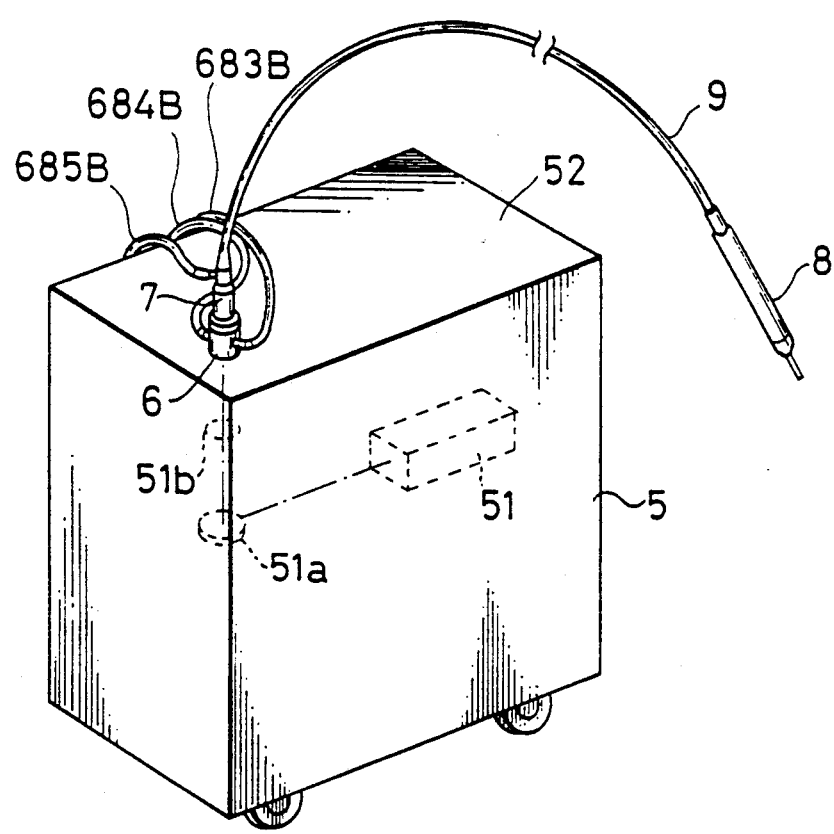
FIG. 7 is a perspective view of another laser treatment device embodying the present invention (hereunder sometimes referred to as a second embodiment) for illustrating the entire configuration thereof.
Figure 8:
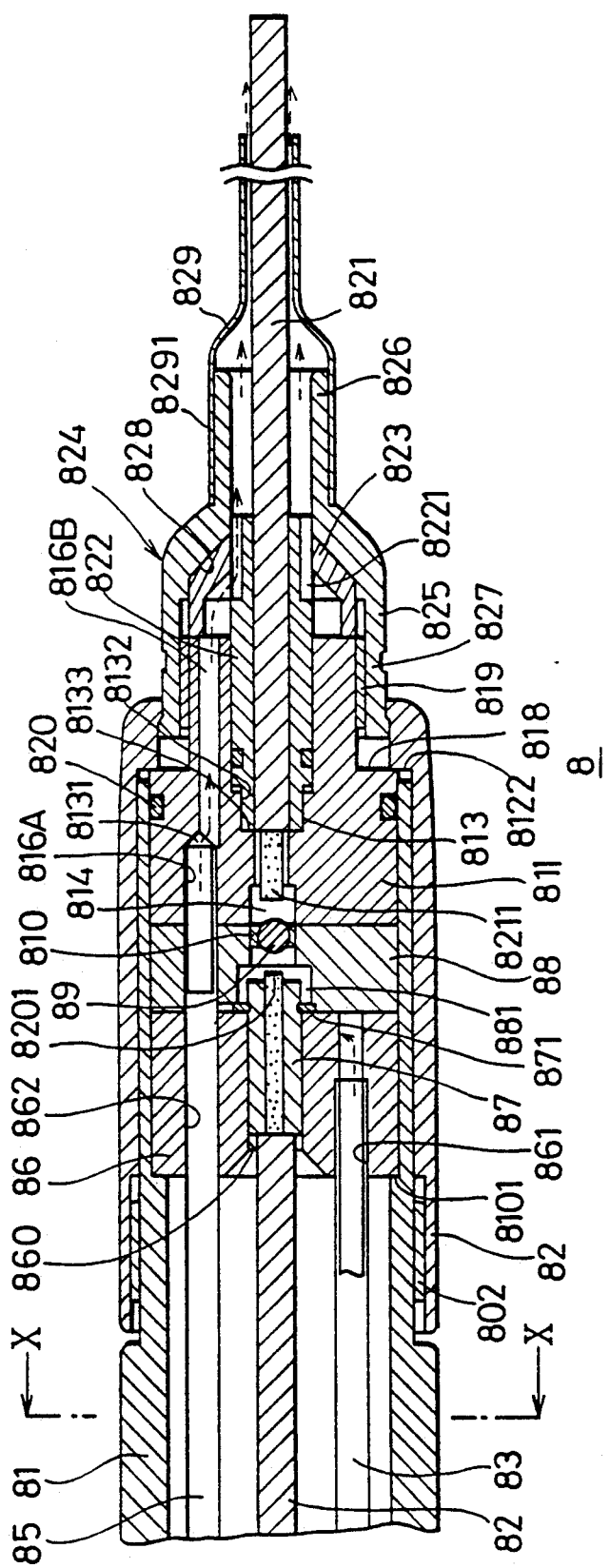
FIG. 8 is a longitudinal sectional view of a laser hand piece 8 of FIG. 7, which is taken along the line VIII—VIII of a transverse sectional view thereof illustrated in FIG. 10.
Figure 9:
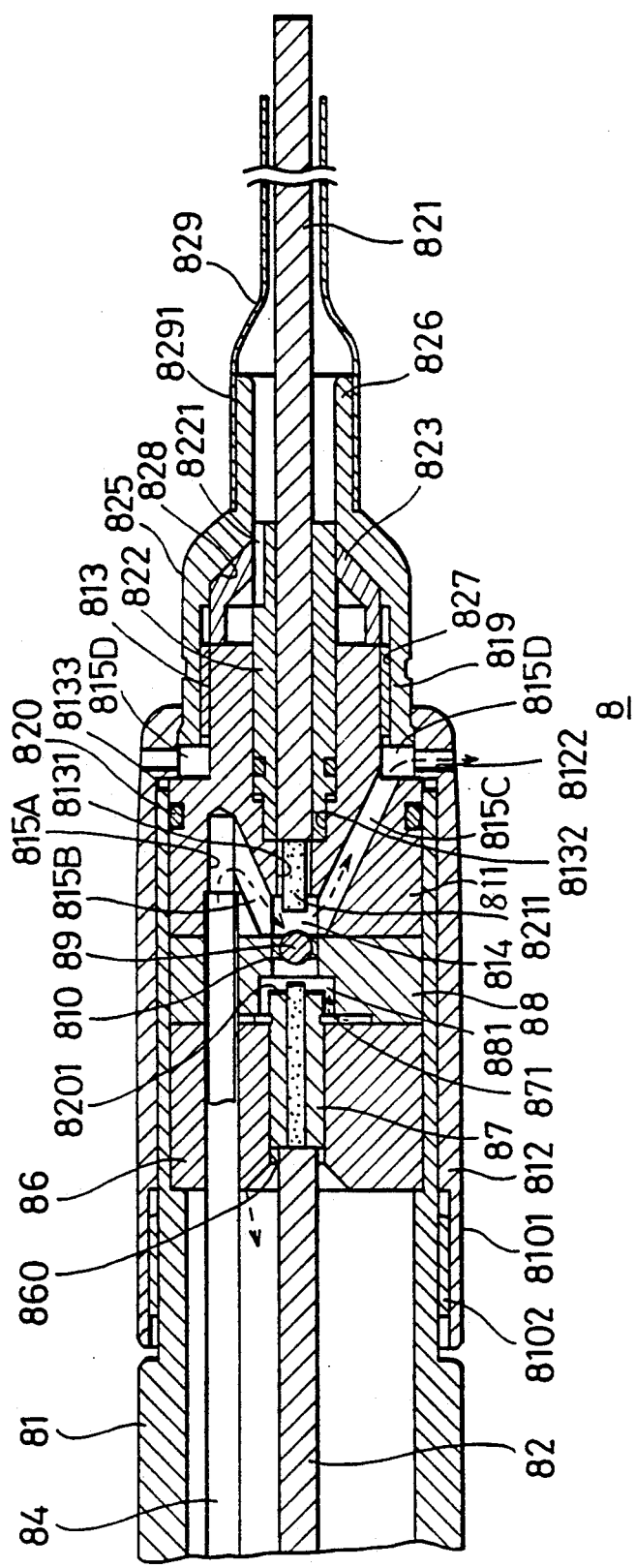
FIG. 9 is a longitudinal sectional view of the laser hand piece 8 of FIG. 7, which is taken along the line IX—IX of the transverse sectional view thereof illustrated in FIG. 10.
Figure 10:
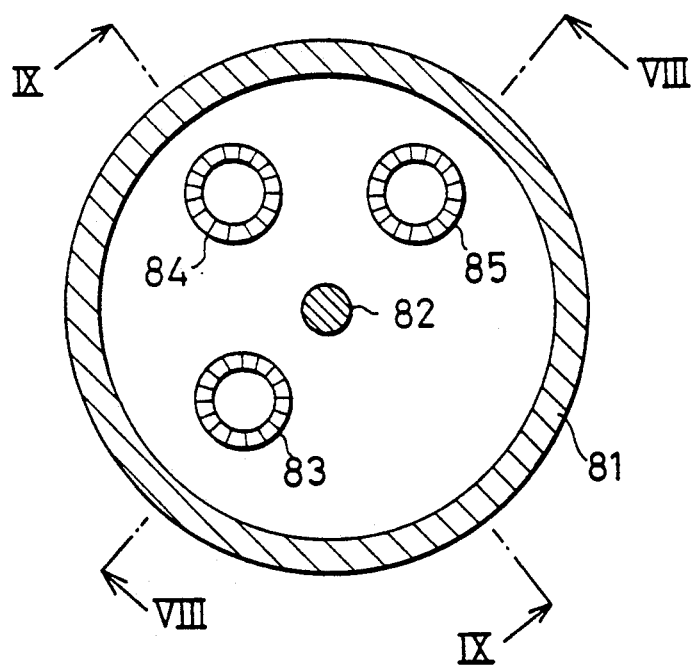
FIG. 10 is a transverse sectional view of the laser hand piece 8 of FIG. 7, which is taken along the line X—X of FIG. 8.
Figure 11:
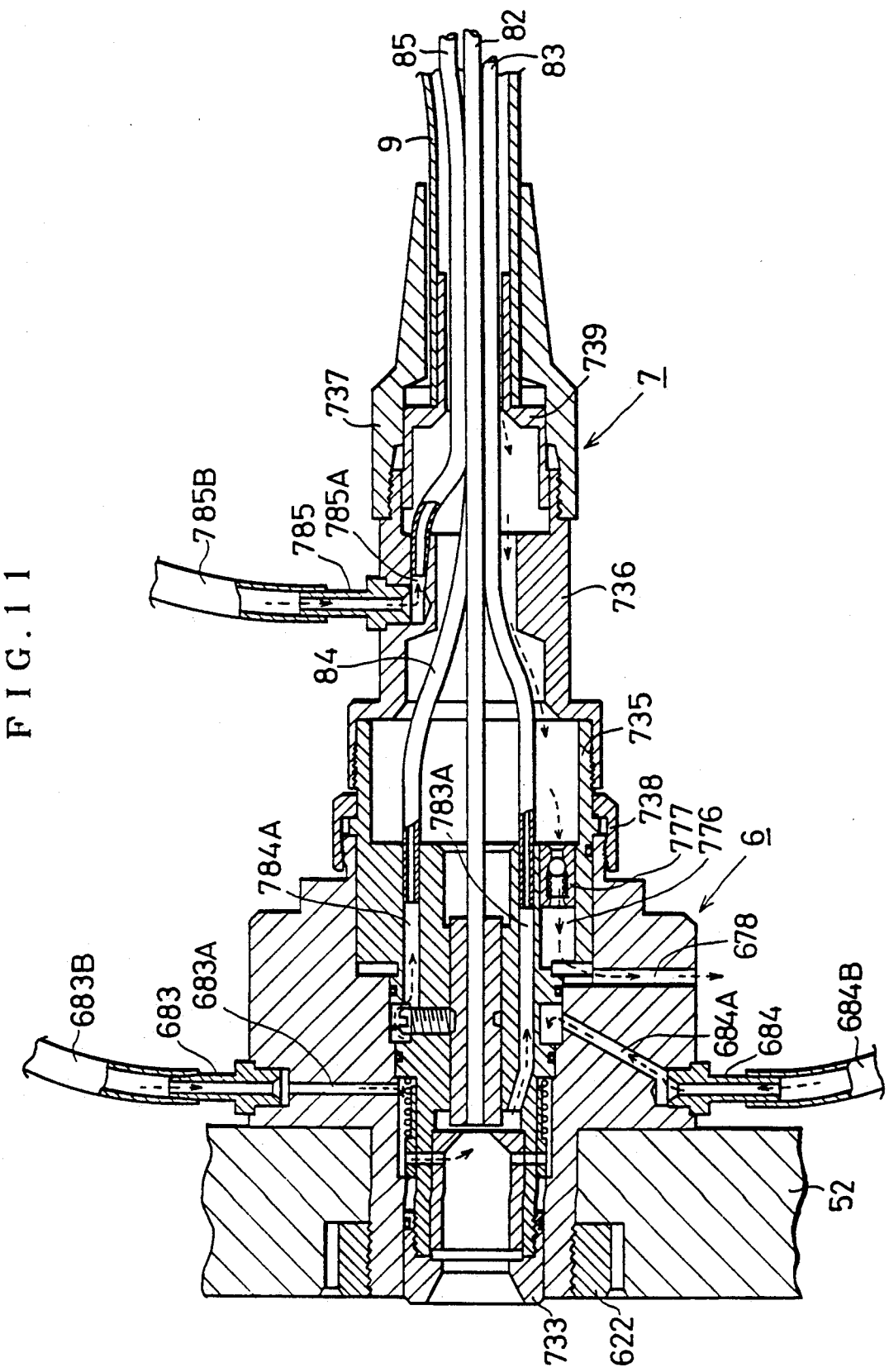
FIG. 11 is a longitudinal sectional view of a socket portion 6 and a connector portion 7 connected thereto of FIG. 7.
Figure 12:
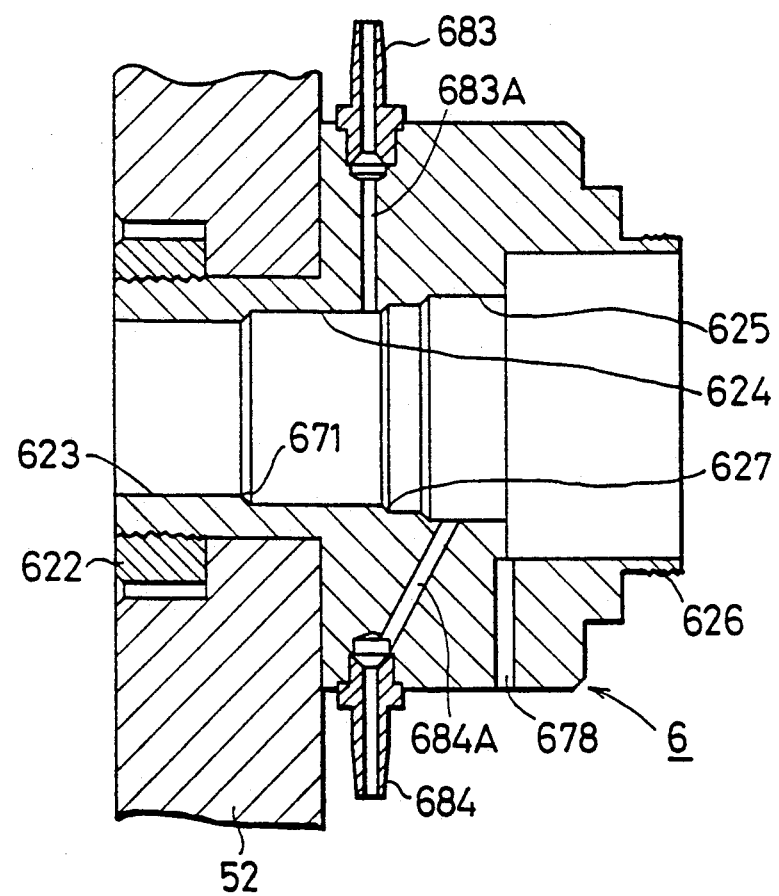
FIG. 12 is a partial longitudinal sectional view of the socket portion 6.

FIG. 7 is a perspective view of another laser treatment device embodying the present invention (namely, the second embodiment) for illustrating the entire configuration thereof. FIG. 8 is a longitudinal sectional view of a laser hand piece 8 of FIG. 7, which is taken along the line VIII—VIII of a transverse sectional view thereof illustrated in FIG. 10. FIG. 9 is a longitudinal sectional view of the laser hand piece 8 of FIG. 7, which is taken along the line IX—IX of the transverse sectional view thereof illustrated in FIG. 10. Further, FIG. 10 is a transverse sectional view of the laser hand piece 8 of FIG. 7, which is taken along the line X—X of FIG. 8. FIG. 11 is a longitudinal sectional view of a socket portion 6 and a connector portion 7 connected thereto of FIG. 7. FIG. 12 is a partial longitudinal sectional view of the socket portion 6. FIG. 13 is a partially cutaway fragmentary-side-view of the connector portion 7 of FIG. 7. Hereinafter, the second embodiment will be described in detail by referring to these figures.

In FIG. 7, reference numeral 5 represents a laser generating device. The socket portion 6, which is portion for emitting laser light, is mounted on the top surface of the laser generating device 5 and is connected to the connector portion 7, to which an end of an armor tube 9 incorporating a laser-light transmitting optical fiber and an aspiration tube or the like is connected. Further, a laser hand piece 8 is connected to the opposite end of the tube 9. Laser light emitted from the laser generating device is led to the laser-light transmitting optical fiber of the tube 9 through the socket portion 6 and the connector portion 7. Then, the laser light led to the optical fiber is transmitted to the laser hand piece 8 by this optical fiber. Incidentally, a laser oscillator 51 is provided in the laser generating device 5. Laser light emitted from the laser oscillator 61 is folded or turned back by a folding mirror 51a. Subsequently, the folded laser light is converged by a converging lens 51b to the socket portion 6 and is thus incident on the laser-light transmitting optical fiber of the connector portion 7. Hereinafter, the laser hand piece 8 will be first described in detail by referring to FIGS. 8 to 10. Further, the socket portion 6 and the connector portion 7 will be described in detail by referring to FIGS. 11 to 14.

(A) Laser Hand Piece 8

As shown in FIGS. 8 to 10, in the laser hand piece 8, an end of each of a laser-light transmitting optical fiber 82, a first aspiration pipe 83, a second aspiration pipe 84 and a water supply pipe 85 is inserted into the body 81 of the laser hand piece 8 on the left or rear end portion of the hand piece 8 and connected with an inner member. Further, a fiber probe 821 is detachably fitted to the opposite side (namely, the tip end) of the laser hand piece 8. Thereby, laser light guided by the optical fiber 82 is emitted from an end of the fiber probe 821. Further, an output end 8201 of the laser-light transmitting optical fiber is cooled by dry gas supplied by the first aspiration pipe 83. Independent of this, an input end 8211 of a fiber probe 821 is cooled by gas fed by the second aspiration pipe 84. Further, washing water supplied by the water supply pipe 85 is spurted from an end of a probe protecting pipe 829. Incidentally, the laser-light transmitting optical fiber 82 is fabricated by coating an optical fiber comprised of a core and a cladding, which are made of fluoride glass, with a protective jacket made of the UV resin. Additionally, an end of each of the fiber 82, the first aspiration pipe 83, the second aspiration pipe 84 and the water supply pipe 85 is airtightly accommodated in the soft flexible armor tube 9. In contrast, the opposite end of each of the fiber 82 and the pipes 83, 84 and 85 is connected to the connector portion 7.

Further, in the inside of the tip portion of the body 8 of the laser hand piece 81, a laser-light transmitting optical-fiber holder 86 is provided in such a fashion to touch a stage 8101 on the inner surface thereof. Moreover, a lens holder 88 is provided on the tip portion of the holder 86. Furthermore, a coupling 811 is provided on the tip portion of the lens holder 88. Incidentally, the holders 86 and 88 and the coupling 811 are fixed between the stage portion 8101 and that of a cover nut 812 by locking the nut 812 to be joined with a screw 8102.

Moreover, a laser-light transmitting optical-fiber terminal, in which a sleeve 87 is adhered by an adhesive to a part of the optical fiber 82 exposed by peeling off the protective jacket, is inserted into a hole 860 of the holder 86. Furthermore, a ring 871 fitted to a groove formed along the circumference of the transverse section of the sleeve 87 on the outer surface thereof is made to touch the end surface of the holder 86. Thereby, a positioning of the output end 8201 of the optical fiber 82 is effected. Even when a twist or distortion occurs between the body 81 of the laser hand piece 8 and the fiber 82 while manipulating the laser hand piece 8, a relative rotation of the holder 86 with respect to the sleeve 87 can prevent a breakage of the fiber 82.

The lens holder 88 has a concave chamber 881 accepting the output end 8201 of the optical fiber 82 therein and a window portion adjoining the chamber 881. A converging spherical lens 89 is fitted to this window portion and supported by an O-ring 810 airtightly. Thus, output cooling chamber 881 and input cooling chamber 814 of the coupling 811 are airtightly separated from each other by the spherical lens 89. Moreover, an interface between the coupling 811 and the body 81 of the laser hand piece 8 is airtightly shut by the 0-ring. Thus a portion for accommodating the optical fiber 82, which is positioned on the left side of the spherical lens 89 as viewed in FIG. 8, is made to be gastight. Consequently, the optical fiber 82 is cut off from moisture included in the open air.

In the coupling 811, a hole 813, into which a probe is inserted, is formed in such a way to communicate with the input cooling chamber 814. This hole 813 has a small-diameter portion 8131, a large-diameter portion 8132 and a stage portion 8133 which is a boundary between the portions 8131 and 8132. In the small-diameter portion 8131, a terminal portion of the fiber probe, which is exposed by peeling off the protective jacket. On the other hand, in the large-diameter portion 8132, a portion of the fiber probe 821, which is coated with the protective jacket, is inserted. Further, an end portion of the terminal sleeve 822 comes in contact with the stage portion 8133. Thus the input end 8211 of the fiber probe 821 is positioned in such a manner to protrude into the input cooling chamber 814 by a suitable length thereof.

The fiber probe 821 is operative to lead laser light guided by the optical fiber 82 to an object and is formed by a short optical fiber. Therefore, it is desirable to use an optical fiber, which has a high moisture-resistance and good mechanical strength (e.g., a breakage-resistance) in comparison with a fluoride fiber even though the efficiency in guiding laser light is low, as the fiber probe 821.

Meanwhile, the output end of the fiber probe sometimes dissolves due to heat generated when irradiated with laser light. Moreover, matters vaporized from tissues at the time of irradiation thereof may adhere to the output end of the fiber probe. Thus it is relatively frequent to exchange the fiber probe for another. Hence, it is preferable that the cost of the fiber probe is low. Consequently, it is preferable to employ an optical fiber, in which a core and a cladding are made of quartz glass and the cladding is coated with metal or heat-proof resin protective-jacket made of, for instance, polyimide resin, as an optical fiber forming the fiber probe 821. However, in view of the fact that it is relatively frequent to exchange the fiber probe for another, a fluoride fiber may be employed.

Although the output end 8201 of the optical fiber 82 and the input end 8211 of the fiber probe 821 are designed and arranged in such a manner that laser light emitted from the output end 8201 is efficiently incident on the input end 8211, a part of the laser light emitted from the output end 8201 becomes changed into heat and thus lost. Thus the output end 8201 is cooled by the dry gas supplied from the first aspiration pipe 83. On the other hand, the input end 8211 is cooled by gas fed from the second aspiration pipe 84. Moreover, by such aspiration, dusts is prevented from adhering to the output end 8201 of the optical fiber 82 and the input end 8211 of the fiber probe 821.

Further, an opening end portion of the first aspiration pipe 83 is inserted into a through hole 861 formed in the holder 86 and is fixed by an adhesive at a part thereof. The dry gas supplied from the pipe 83, which is usually dry air, flows into the output cooling chamber 881 through a space between the holders 86 and 88 so as to cool the output end 8201 of the optical fiber 82. Then, the gas entered the chamber 881 further flows into a space among the body 81, the optical fiber 82 and the pipes 83, 84 and 85 through another space provided between a hole 862 in the holder 86 and the water supply pipe 85. Furthermore, as viewed in FIG. 8, the gas goes upstream to the left and is exhausted from a gas exhaust port 678 (see FIGS. 11 and 12), which is apart from the output end 8201 a sufficient distance, through the armor tube 9. Incidentally, a check valve 777 is provided just prior to the port 678 in order to prevent a moist open air from infiltrating into the tube 9.

As described above, the dry gas supplied from the first aspiration pipe 83 flows upstream in the portion accommodating the laser-light transmitting optical-fiber after cooling the output end 8201 of the optical fiber 82. Finally, the gas is output from a port which is sufficiently apart from the output end 8201. Thus the dry gas flowing backward serves to cut the optical fiber 82 off from a moist and cool the optical fiber 82. In addition, even if the optical fiber 82 is broken and is destroyed by fire due to the fact that the fiber 82 is made of a fluoride fiber and thus has a low breakage-resistance, fragments (or dusts) and smoke are swept away by the dry gas and are eventually exhausted from the place or port sufficiently distant from the output end 8201. Thus the spherical lens 89 is prevented from being stained with the dusts and smoke. Moreover, the fragments and smoke are prevented from adhering to a diseased part. Furthermore, a patient is prevented from being frightened. In case of this embodiment, it is preferable from such a point of view to position the exhaust port for exhausting the dry gas supplied from the pipe 83 at a place sufficiently distant from the output end 8201.

The second aspiration pipe 84 for supplying gas to be used to cool the input end 8211 of the fiber probe is inserted into a hole 815A formed in the coupling 811 through the holders 86 and 88. Further, the pipe 84 is fixed to the hand piece at an opening end thereof by an adhesive. The gas supplied from the pipe 84, which is usually air, flows into the input cooling chamber 814 through a ventilation passage 815A from the hole 815A and cools the input end 8211. Further, the gas having flowed into the input cooling chamber 814 further goes to a gas outputting path 815D through a gas guiding path 815C and finally is exhausted from a gas exhaust port 8122 provided in the cover nut 812.

The coupling 811 has a small-diameter portion, on the outer surface of the tip or right end of which a screw thread 819 is formed. Further, a stage portion 818, which is formed at a boundary between the small-diameter portion and the large-diameter portion of the coupling 811, comes in contact with the port 8122 of the cover nut when the screw of the cover nut is put on.

Thus the coupling 811 is fixed to the body of the laser hand piece 8 as above described.

Reference numeral 824 designates a cylindrical probe holder. Further, a screw 827 formed in the inner surface of a large-diameter portion 825 is joined with the screw 819 formed on the coupling 811. Moreover, a taper portion 828 formed in the inside of the holder 824 has a tapered surface at an end thereof and is engaged with a clamper 823, which touches the outer end surface of the coupling 811, at another end thereof. If the screw 827 of the holder 824 is driven and the holder 824 is moved to the left as viewed in FIG. 8, the taper portion 828 is pressed against the tapered surface of the clamper 823. Thereby, the clamper 823 is deformed toward the inside of the hand piece so as to clamp and hold a terminal sleeve 822 of the fiber probe. Further, if the screw 827 of the holder 824 is loosened, the sleeve 822 is released from the clamping by the clamper 823. Thus the fiber probe 821, on the outer surface of which the sleeve 822 is mounted, can be freely fitted and detached by driving and loosening the screw 827 of the holder 824.

Further, the end surface of a small-diameter portion 826 provided on the tip or right side of the holder 824 is shaped like a polygon (e.g., a hexagon) and is covered with a polygonal base portion 8291 of the probe protecting pipe 829. The water supply pipe 85 penetrates the holders 86 and 88 and is inserted into a hole 816A bored in the coupling 811. Incidentally, the opening end portion of the pipe 85 is fixed by an adhesive to the coupling. The right end of the hole 816A communicates with a water guiding passage 816B.

The water supplied from the pipe 86, which may be a solution of salt or water spray, flows into a space formed between the small-diameter portion 826 of the holder 824 and the fiber probe 821 through the passage 816B, a space on the left side of the clamper 823 and a groove 8221, which is partially cutaway in the longitudinal direction and is provided on the tip or right side of the sleeve 822. Then, the water flows along the fiber probe 821 within the probe protecting pipe 829 and is spurted from an end of the pipe 829 toward a tooth. Thus remaining matters, which adhere to the tooth and the vicinity thereof, are washed and eliminated. Simultaneously, the end of the fiber probe 821 is also washed. Incidentally, the water flowing along the fiber probe 821 can cool the fiber probe 821.

In the foregoing description of the embodiments, it has been described that the optical fiber 82 is made of a fluoride fiber. The material of the optical fiber 82, however, is not limited to the fluoride fiber. The present invention can be applied not only to a case where an optical fiber, which is liable to the influence of water or moisture and has a low moisture-resistance, is employed as the laser-light transmitting optical fiber, but also to a case where it is intended that a relatively long laser-light transmitting optical fiber for guiding laser light emitted from a laser light source to a laser treatment device such as a laser hand piece is protected from moisture and the life span of the optical fiber is elongated. Furthermore, the probe is not limited to the fiber probe. The laser treatment device of the present invention is not limited to the laser hand piece. Further, various modifications of the embodiments can be realized. For example, in case of an modification of the embodiment of FIGS. 8 and 9, the inner diameter portion of the laser hand piece may be used as a ventilation path. Further, an optical fiber, which can efficiently guide laser light, may be employed without misgiving or caring a water-proof or moisture-resistance thereof. Dry gas is not necessarily employed as a gas for cooling the input end of the probe, which is supplied from the second aspiration pipe or passage 84. Additionally, a transparent plate capable of transmitting laser light may be employed as the spherical lens 89.

(B) Socket Portion 6 and Connector Portion 7

Next, the socket portion 6 mounted on the top surface 62 of the laser generating device, as well as the connector portion 7 connected to the socket portion 6, will be described in detail hereinbelow by referring to FIGS. 11 to 14. Incidentally, the socket portion 6 is arranged and fixed on the top surface 52 of the laser generating device 62 in such a manner that the longitudinal central axis of the hollow of the socket portion 6 corresponds to the optical axis of the laser oscillator 51 in a coaxial manner. Further, two gas introducing ports 683 and 684 for inputting gas into the hollow of the socket portion 6 are formed in the peripheral part of the portion 6. Moreover, an introducing port 785 for inputting washing water is formed in the peripheral part of the connector portion 7.

The connector portion 7 has the body 71 of the connector and a connection fitting 736 screwed and fixed to a cylinder portion 735 in front of (namely, on the right side of) the body 71. Further, an end of the armor tube 9 is connected and fixed to the front side of the connection fitting airtightly. Incidentally, the armor tube 9 incorporates the first aspiration pipe 83, the second aspiration pipe 84 and the water supply pipe 85. An end of each of these pipes is connected to the connector portion 7.

Moreover, the optical fiber 82 connected to the laser hand piece 8 is inserted into and fixed to the body 71 of the connector portion through a ferrule 762. Furthermore, a portion facing the input end surface 820 of the optical fiber 82 is adapted to transmit laser light supplied from an external device to the input end surface 820. Namely, an opening portion 741, which is open to the rear side (namely, the left side, as viewed in FIG. 14) thereof, is provided in the rear end portion (namely, the left end portion) of the connector portion 7. A space present in front of (namely, on the right side of) the opening portion 741 is airtightly partitioned by a transparent partition plate 7411. Thus a space formed between the partition plate 7411 and the input end surface 820 of the optical fiber 82 is used as a cooling chamber 740 to be used for cooling the input end surface 820 of the optical fiber 82.

The partition plate 7411 intervenes between a cylindrical end fixing fitting 733, which is screwed to the end of a front cylinder portion 732 of the connector portion 7, and an inner cylinder member 734, which is screwed onto the inner peripheral surface of the portion 732. This member 734 has a nozzle portion 742, the outer surface of which is tapered and is positioned in front of the input end surface 820 of the optical fiber 82.

The cooling chamber 740 communicates with the outside through holes 753 which penetrate the member 734 and the portion 732 and is open to the outside. The hole 753 is usually closed by the inner surface of a circular valve 773 fitted to the portion 732. The valve 773 is mounted on the outer peripheral surface of the portion 732 in such a way that the inner surface of the valve 773 can slide on the peripheral surface of the portion 732. Moreover, the valve 773 is elastically forced to the rear side (namely, the left side as viewed in FIG. 14) by a compression spring 774. When a valve body 773A is forced forward, a valve hole 773A is made to communicate with the hole 753. Further, the cooling chamber 740 communicates with the pipe 83 through a path 783 formed in such a manner to penetrate the body 71 of the connector portion in the longitudinal direction.

Further, the connector portion 7 is connected to the socket portion 6 in such a manner that the outer peripheral surface of the body 71 of the connector portion comes in contact with the inner peripheral surface of acceptance holes 623 and 624 of the socket portion 6. Moreover, a first stage portion 671 is formed on the inner peripheral surface of the socket portion 6. Furthermore, a rear end portion 772 of the valve body 773 of the connector portion 77 is adapted to touch the first stage portion 671.

As illustrated in FIG. 11, when the connector portion 7 is fitted to the socket portion 6, a cap nut 738 of the connector portion 7 is screwed and fixedly positioned to the edge screw portion 626 of the socket portion 6 in such a fashion that a second stage portion 627 provided in the inner surface of the hollow of the socket portion 6 is in contact with a stage portion 739 (see FIG. 14) provided on the outer peripheral surface of the connector portion 7. The outer peripheral surface of the fitting 733 of the connector portion 7 is slidably fitted to the rear inner peripheral surface (623) of the socket portion 6 so that the optical axis of the laser oscillator 51 is in agreement with the central axis of the body 71 of the connector portion 7. Laser light is transmitted by the transparent partition plate 7411 and is then converged onto and incident on the input end surface 820 of the optical fiber 82 accurately. Subsequently, the laser light impinged thereon is transmitted by the optical fiber 82 and is further supplied to the laser hand piece 8. Finally, the laser light is radiated from the end of the fiber probe 821.

When connected to the connector portion 7, the stage portion 671 of the socket portion 6 pushes back the valve body 773 fitted to the outer peripheral surface of the connector portion 7 against the elastic force of the spring 774. As the result, the hole 773A of the valve 773 comes to communicate with the hole 753 which is open to the portion 732 and the member 734. If, in such a state, pressurized dry gas supplied from a pipe 683B through the port 683 is input, the gas flows into the chamber 740 through a gas passage 683A, a gap formed between the inner peripheral surface 624 of the socket portion 6 and the outer peripheral surface of the valve 773 and the holes 773 and 753. Then, the gas is shot up to the input end surface 820 of the fiber 82 from the nozzle portion 742 to cool the input end of the fiber 82. Thereafter, the dry gas is sent into the hand piece 8 by way of a gas passage 783A and the pipe 83. When it reaches the chamber 881 of the hand piece 8, the gas cools the output end 8201 of the optical fiber 82. Thereafter, the dry gas is exhausted to the armor tube 9. Subsequently to this, the gas goes backward in the tube 9 and finally is exhausted to the outside from the port 678 of the portion 6 through the valve 777 provided at the port 776 of the portion 7.

Thereby, in the case where a fiber made of a hygroscopic material (e.g., a fluoride fiber) is used as the optical fiber 82, ambient air touching the input and output end and the outer peripheral surface of the optical fiber 82 is made to be dry air substantially including no moisture. Incidentally, appropriate means (e.g., an O-ring) for keeping regions, which should be airtight, (e.g., a connection part between the socket portion 6 and the connector portion 7) airtight are used.

Moreover, if air supplied from the pipe 684B through the port 684 is input, the air is led to the laser hand piece 8 through the passages 684A and 784A and the pipe 84. Subsequently to this, the air cools the input end 8211 of the fiber probe 821 as described above.

Furthermore, if washing water fed from the pipe 785B through the port 785, the water is led to the hand piece 8 by way of the passages 784A and the pipe 85. Thereafter, the water is spurted from the end of the probe 821 as stated above.

Incidentally, inner and outer clamping fittings 737 (and 739) are provided to the front end of the connection fitting 736 fixed to the portion 735 of the body 71. Thereby, an end of the armor tube 9 is airtightly connected and fixed to the connector portion 7.

In case of this embodiment, the output end 8201 and the input end 820 of the optical fiber 82 and the input end 8211 of the probe 821 can be cooled by different refrigerants independently of one another. Thus, the fiber probe 821 can be exchanged for another while causes for exerting the influence of moisture on the optical fibers are being eliminated by cooling the output end 8201 and the input end of the optical fiber 82 by using dry gas and by cooling the input end 8211 of the probe 821 by using ordinary air by another cooling system. Additionally, washing water can be spurted from the end of the probe 821. Consequently, a medical treatment can be achieved performing a washing of a diseased part to be treated.

While preferred embodiments of the present invention have been described above, it is to be understood, as previously stated, that the present invention is not limited thereto and that other modifications will be apparent to those skilled in the art without departing from the spirit of the invention. The scope of the present invention, therefore, is to be determined solely by the appended claims.

What is claimed is:

1. A laser treatment device, comprising:
  a laser light source;
  a laser-light transmitting optical fiber coupled to the laser light source; and
  a probe coupled to the laser-light transmitting optical fiber wherein the probe comprises a laser-light guiding optical fiber separated from the laser-light transmitting optical fiber, said probe comprising a cooling chamber for cooling optical fibers, a refrigerant supply path for supplying a refrigerant to the cooling chamber, and a refrigerant discharge path for discharging a refrigerant from the cooling chamber, said cooling chamber, refrigerant supply path and refrigerant discharge path disposed in the vicinity of an output end of the laser-light transmitting optical fiber and an input end of the laser-light guiding optical fiber, the transmitted laser light being output from said laser-light transmitting optical fiber and input to the laser-light guiding optical fiber, the output end of the laser-light guiding optical fiber, the output end of the laser-light transmitting optical fiber and the input end of the probe being cooled by the refrigerant supplied to the cooling chamber through the refrigerant supply path, wherein the input end of the laser-light guiding optical fiber is protruded from an inner surface of the cooling chamber, and wherein the outer diameter of the input end of the probe is set equal to or less than that of the output end of the laser-light transmitting optical fiber.

2. The laser treatment device according to claim 1, wherein a transmittable member is provided between the input end of the probe and the output end of the laser-light transmitting optical-fiber, the cooling chamber being partitioned into a first cooling sub-chamber for cooling the input end of the probe and a second cooling sub-chamber for cooling the output end of the laser-light transmitting optical-fiber, wherein the first cooling sub-chamber is connected to a first feed path for feeding a first refrigerant thereto and a first exhaust path for discharging a first refrigerant therefrom, and the second cooling sub-chamber is connected to a second feed path for feeding a second refrigerant thereto and a second exhaust path for discharging a second refrigerant therefrom, the input end of the probe and the output end of the light transmitting optical-fiber being cooled by the first refrigerant and the second refrigerant, respectively.

3. The laser treatment device according to claim 2, wherein said transmittable member is a light-converging member for converging laser light output from the output end of the laser-light transmitting optical-fiber to the input end of the laser-light guiding optical fiber.

4. The laser treatment device according to claim 2, wherein a part of a cladding of the input end of the laser-light guiding optical fiber and a part of a cladding of the output end of the laser-light transmitting optical-fiber are exposed, wherein the exposed part of the cladding of the input end of the laser-light guiding optical fiber protrudes into the first cooling chamber and wherein the exposed part of the cladding of the output end of the laser-light transmitting optical-fiber protrudes into the second cooling chamber.

5. The laser treatment device according to claim 1, wherein cooling chamber for cooling an input end of the laser-light transmitting optical fiber is further provided on the surface of the input end of the laser-light transmitting optical fiber.

6. The laser treatment device according to claim 1, further comprising a liquid guiding member for letting liquid flow along the probe and spurting the liquid from the vicinity of an end of the probe in such a manner to cover an outer peripheral portion of the probe, the laser treatment device further comprising a liquid feeding member for supplying liquid to the liquid guiding member.

7. The laser treatment device according to claim 1, further comprising a probe angle regulating member for fixedly turning the probe in an arbitrary direction.

8. The laser treatment device according to claim 7, wherein the probe angle regulating member is more flexible than the probe.

9. The laser treatment device according to claim 1, wherein the laser light source is an Er:YAG laser.

10. The laser treatment device according to claim 1, wherein the probe is detachably secured to the laser-light transmitting optical-fiber.

11. The laser treatment device according to claim 1, wherein the probe is coated with a protective jacket made of a material which has high heat-resistance and mechanical strength.

* * * * *

UNITED STATES PATENT AND TRADEMARK OFFICE
CERTIFICATE OF CORRECTION

PATENT NO. : 5,300,067
DATED : April 5, 1994
INVENTOR(S) : Sadahiro NAKAJIMA, Naoshi ENDOH, Kenzo KATAOKA, Masaki ODAKA and Yoshihide OKAGAMI It is certified that error appears in the above-indentified patent and that said Letters Patent is hereby corrected as shown below:

ON THE COVER PAGE:

change "[73] Assignee: Hoya Corporation, Tokyo, Japan" to
—[73] Assignees: Hoya Corporation, Tokyo, Japan and
Kabushiki Kaisha Morita Seisakusho, Kyoto-shi, Japan—

Signed and Sealed this

Twenty-fifth Day of October, 1994

Attest:

BRUCE LEHMAN

Attesting Officer    Commissioner of Patents and Trademarks